US008440211B2

(12) United States Patent
Auguste

(10) Patent No.: US 8,440,211 B2
(45) Date of Patent: May 14, 2013

(54) COSMETIC COMPOSITION COMPRISING A VOLATILE FATTY PHASE

(75) Inventor: Fr'déric Auguste, Chevilly-Larue (FR)

(73) Assignee: L'Oreal S.A., Paris (FR)

( * ) Notice: Subject to any disclaimer, the term of this patent is extended or adjusted under 35 U.S.C. 154(b) by 729 days.

(21) Appl. No.: 12/277,742

(22) Filed: Nov. 25, 2008

(65) Prior Publication Data

US 2009/0074689 A1   Mar. 19, 2009

Related U.S. Application Data

(63) Continuation of application No. 10/443,793, filed on May 23, 2003, now abandoned.

(60) Provisional application No. 60/461,400, filed on Apr. 10, 2003.

(30) Foreign Application Priority Data

Apr. 4, 2003 (FR) ..................................... 03 04259
May 20, 2003 (FR) ..................................... 03 06068

(51) Int. Cl.
*A61K 8/02* (2006.01)

(52) U.S. Cl.
USPC ........................................................ 424/401

(58) Field of Classification Search ........................ None
See application file for complete search history.

(56) References Cited

U.S. PATENT DOCUMENTS

| | | | |
|---|---|---|---|
| 6,338,839 B1 | 1/2002 | Auguste et al. | |
| 6,432,912 B1 | 8/2002 | Rodelet | |
| 6,534,072 B2 * | 3/2003 | Mondet et al. | 424/401 |
| 2001/0053377 A1 | 12/2001 | Mondet et al. | |
| 2003/0072730 A1 | 4/2003 | Tournilhac et al. | |
| 2004/0126336 A1 | 7/2004 | Hansenne et al. | |
| 2005/0069564 A1 | 3/2005 | Eversheim et al. | |

FOREIGN PATENT DOCUMENTS

| | | |
|---|---|---|
| DE | 43 41 652 | 6/1994 |
| EP | 0 333 433 | 9/1989 |
| EP | 0 979 646 | 2/2000 |
| EP | 1 010 716 | 7/2000 |
| EP | 1 043 015 | 10/2000 |
| EP | 1 213 006 | 6/2002 |
| EP | 1 607 081 | 12/2005 |
| FR | 2 825 915 | 12/2002 |
| JP | 61-065809 | 4/1986 |
| JP | 61-161202 | 7/1986 |
| JP | 61-161209 | 7/1986 |
| JP | 61-161211 | 7/1986 |
| JP | 61-161214 | 7/1986 |
| JP | 63-183516 | 7/1988 |
| JP | 3-157317 | 7/1991 |
| JP | 3-193718 | 8/1991 |
| JP | 6-199640 | 7/1994 |
| JP | 8-157324 | 6/1996 |
| JP | 9-020620 | 1/1997 |
| JP | 2000-119120 | 4/2000 |
| JP | 2000-212445 | 8/2000 |
| JP | 2002-370919 | 12/2002 |
| JP | 2003-503327 | 1/2003 |
| JP | 2005-503733 | 2/2005 |
| JP | 2005-509041 | 4/2005 |
| WO | WO 96/06594 | 3/1996 |
| WO | WO 01/00141 | 1/2001 |
| WO | WO 01/15658 | 3/2001 |
| WO | WO 03/013447 | 2/2003 |
| WO | WO 03/042221 | 3/2003 |
| WO | WO 2004/082644 | 9/2004 |

OTHER PUBLICATIONS

French Search Report for FR 03/06068 (corresponding to the present application) dated Jan. 29, 2004, p. 1-2.
European Search Report for EP 11 17 5076, dated Sep. 9, 2011.

* cited by examiner

*Primary Examiner* — Carlos Azpuru
(74) *Attorney, Agent, or Firm* — Oblon, Spivak, McClelland, Maier & Neustadt, L.L.P.

(57) ABSTRACT

The invention relates to a composition comprising, in a physiologically acceptable medium, a volatile silicone fatty phase comprising at least one non-cyclic volatile silicone oil, wherein the volatile silicone fatty phase has an evaporation profile such that the mass of the at least one volatile silicone oil evaporated after 30 minutes is from 2 mg/cm$^2$ to 9 mg/cm$^2$. The invention also relates to making up and caring for human keratin materials using the inventive compositions.

29 Claims, No Drawings

COSMETIC COMPOSITION COMPRISING A VOLATILE FATTY PHASE

This application is a continuation of U.S. patent application Ser. No. 10/443,793, filed May 23, 2003, which claims benefit of U.S. Provisional Application No. 60/461,400, filed Apr. 10, 2003, French Patent Application No. 03 04259, filed on Apr. 4, 2003, and French Patent Application No. 03 06068, filed on May 20, 2003, all of which are incorporated herein by reference.

Disclosed herein is a cosmetic composition comprising at least one volatile silicone oil. Further disclosed herein is a non-therapeutic care or make-up process for human keratin materials, comprising applying the composition to the keratin materials.

Volatile silicone oils are commonly used in cosmetic compositions for their good cosmetic properties, such as their pleasant feel on contact with the skin. These oils may also evaporate quickly after they have been applied to keratin materials. However, if their rate of evaporation is too high, the user may not have sufficient time to apply the cosmetic product to the keratin materials, or sufficient time to apply the cosmetic product to the keratin materials uniformly.

The volatile silicone oils most commonly used in cosmetic products are cyclic silicones containing from 4 to 6 siloxane groups (generally known as D4, D5 and D6) and containing only methyl groups.

Disclosed herein is an alternative for formulating compositions comprising volatile oils, such as volatile oils that are compatible with the ingredients usually used in cosmetic compositions.

The inventor has discovered that such a composition may be obtained by using at least one particular volatile silicone oil that may give the volatile fatty phase a particular evaporation profile.

Disclosed herein is a composition comprising, in a physiologically acceptable medium, a volatile silicone fatty phase comprising at least one non-cyclic volatile silicone oil, wherein the volatilesilicone fatty phase has an evaporation profile such that the mass of the at least one non-cyclic volatile silicone oil evaporated after 30 minutes ranges from 2 mg/cm$^2$ to 9 mg/cm$^2$.

Further disclosed herein is a composition comprising, in a physiologically acceptable medium, a volatile fatty phase comprising at least one non-cyclic volatile oil with a surface tension of less than 21 mN/m, such as less than 20 mN/m, wherein the volatile fatty phase has an evaporation profile such that the mass of the at least one non-cyclic volatile oil evaporated after 30 minutes ranges from 2 mg/cm$^2$ to 9 mg/cm$^2$.

Even further disclosed herein is a cosmetic make-up process or non-therapeutic treatment process for a keratin material, comprising applying to the keratin material a composition as defined above.

The term "volatile oil" means an oil (or a non-aqueous medium) that may evaporate on contact with the skin in less than one hour at room temperature and atmospheric pressure. The volatile oil may be a volatile cosmetic oil, which is liquid at room temperature, which may, for example, have a non-zero vapour pressure, at room temperature and atmospheric pressure, or may have a vapour pressure ranging, for example, from 0.13 Pa to 40 000 Pa (10$^{-3}$ to 300 mmHg), further, for example, from 1.3 Pa to 13 000 Pa (0.01 to 100 mmHg), such as from 1.3 Pa to 1300 Pa (0.01 to 10 mmHg).

The composition disclosed herein comprises a physiologically acceptable medium, such as a cosmetically or dermatologically acceptable medium, i.e., a medium that is compatible with keratin materials such as the skin, mucous membranes, the hair, the eyelashes, the eyebrows and the nails.

The composition disclosed herein comprises a volatile silicone fatty phase comprising at least one non-cyclic volatile silicone oil, wherein the volatile silicone fatty phase has an evaporation profile such that the mass of the at least one non-cyclic volatile silicone oil evaporated after 30 minutes ranges from 2 mg/cm$^2$ to 9 mg/cm$^2$, such as from 2 mg/cm$^2$ to 8 mg/cm$^2$, from 2 mg/cm$^2$ to 7 mg/cm$^2$, from 2.3 mg/cm$^2$ to 6 mg/cm$^2$, from 3 mg/cm$^2$ to 5.5 mg/cm$^2$, or from 3 mg/cm$^2$ to 4.7 mg/cm$^2$.

The evaporation rate of the oil is measured according to the protocol described below.

Moreover, in one embodiment, the composition comprises a volatile fatty phase comprising at least one non-cyclic volatile oil with a surface tension of less than 21 mN/m, such as less than 20 mN/m, wherein the volatile fatty phase has an evaporation profile such that the mass of the at least one non-cyclic volatile oil evaporated after 30 minutes ranges from 2 mg/cm$^2$ to 9 mg/cm$^2$, such as from 2 mg/cm$^2$ to 8 mg/cm$^2$, from 2 mg/cm$^2$ to 7 mg/cm$^2$, from 2.3 mg/cm$^2$ to 6 mg/cm$^2$, from 3 mg/cm$^2$ to 5.5 mg/cm$^2$, or from 3 mg/cm$^2$ to 4.7 mg/cm$^2$.

Such a non-cyclic volatile oil is chosen, for example, from non-cyclic volatile silicone oils.

The surface tension of a volatile oil is measured according to the protocol described below.

The non-cyclic volatile silicone oil may be chosen from linear and branched volatile silicone oils.

The non-cyclic volatile silicone oil may be chosen, for example, from:

the non-cyclic linear silicones of formula (I):

$$(R)_3SiO\text{---}((R)_2SiO)_n\text{---}Si(R)_3 \quad (I)$$

in which R, which may be identical or different, is chosen from:

saturated and unsaturated hydrocarbon-based radicals comprising from 1 to 10 carbon atoms, such as from 1 to 6 carbon atoms, optionally substituted with at least one substituent chosen from a fluorine atom and a hydroxyl group, and a hydroxyl group, wherein one of the radicals R may be a phenyl group, and n is an integer ranging from 0 to 8, such as from 2 to 6 and further such as from 3 to 5, and wherein the silicone compound of formula (I) comprises not more than 18 carbon atoms, such as not more than 17 carbon atoms, not more than 16 carbon atoms, or not more than 15 carbon atoms;

the branched silicones of formulae (II) and (III) below:

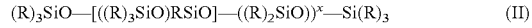

$$(R)_3SiO\text{---}[((R)_3SiO)RSiO]\text{---}((R)_2SiO))_x\text{---}Si(R)_3 \quad (II)$$

$$[(R)_3SiO]_4Si \quad (III)$$

in which R, which may be identical or different, is chosen from:

saturated and unsaturated hydrocarbon-based radicals comprising from 1 to 10 carbon atoms, optionally substituted with at least one substituent chosen from a fluorine atom and a hydroxyl group, and a hydroxyl group, wherein one of the radicals R may be a phenyl group, and x is an integer ranging from 0 to 8, and wherein the silicone compound of formula (II) or (III) comprises not more than 18 carbon atoms, such as not more than 17 carbon atoms, not more than 16 carbon atoms, or not more than 15 carbon atoms.

For the silicones of formulae (I), (II) and (III), the ratio of the number of carbon atoms to the number of silicone atoms may range from 2.25:1 to 4.33:1.

The silicones of formulae (I) to (III) may be prepared according to the known processes for synthesizing silicone compounds.

When the volatile silicone by itself has the evaporation profile as defined above for the volatile fatty phase, it may be present as sole volatile silicone oil in the composition, and may, for example, constitute the entire volatile phase of the composition.

When the volatile silicone does not by itself have the evaporation profile as defined above for the volatile fatty phase, it is then used as a mixture with another volatile silicone that has an evaporation profile in accordance with that described above, such that the mixture of volatile silicones has said evaporation profile.

Examples of non-cyclic volatile silicones that may be used are given below; these silicones may be used alone or as a mixture so as to obtain the evaporation profile defined above.

Among the silicones of formula (I) that may be mentioned are, for example:

a) the following disiloxanes:
hexamethyldisiloxane (surface tension=15.9 mN/m), sold, for example, under the name DC 200 Fluid 0.65 cst by the company Dow Corning;
1,3-di-tert-butyl-1,1,3,3-tetramethyldisiloxane;
1,3-dipropyl-1,1,3,3-tetramethyldisiloxane;
heptylpentamethyldisiloxane;
1,1,1-triethyl-3,3,3-trimethyldisiloxane;
hexaethyldisiloxane;
1,1,3,3-tetramethyl-1,3-bis(2-methylpropyl)disiloxane;
pentamethyloctyldisiloxane;
1,1,1-trimethyl-3,3,3-tris(1-methylethyl)disiloxane;
1-butyl-3-ethyl-1,1,3-trimethyl-3-propyldisiloxane;
pentamethylpentyldisiloxane;
1-butyl-1,1,3,3-tetramethyl-3-(1-methylethyl)disiloxane;
1,1,3,3-tetramethyl-1,3-bis(1-methylpropyl)disiloxane;
1,1,3-triethyl-1,3,3-tripropyldisiloxane;
(3,3-dimethylbutyl)pentamethyldisiloxane;
(3-methylbutyl)pentamethyldisiloxane;
(3-methylpentyl)pentamethyldisiloxane;
1,1,1-triethyl-3,3-dimethyl-3-propyldisiloxane;
1-(1,1-dimethylethyl)-1,1,3,3,3-pentamethyldisiloxane;
1,1,1-trimethyl-3,3,3-tripropyldisiloxane;
1,3-dimethyl-1,1,3,3-tetrakis(1-methylethyl)disiloxane;
1,1-dibutyl-1,3,3,3-tetramethyldisiloxane;
1,1,3,3-tetramethyl-1,3-bis(1-methylethyl)disiloxane;
1,1,1,3-tetramethyl-3,3-bis(1-methylethyl)disiloxane;
1,1,1,3-tetramethyl-3,3-dipropyldisiloxane;
1,1,3,3-tetramethyl-1,3-bis(3-methylbutyl)disiloxane;
butylpentamethyldisiloxane;
pentaethylmethyldisiloxane;
1,1,3,3-tetramethyl-1,3-dipentyldisiloxane;
1,3-dimethyl-1,1,3,3-tetrapropyldisiloxane;
1,1,1,3-tetraethyl-3,3-dimethyldisiloxane;
1,1,1-triethyl-3,3,3-tripropyldisiloxane;
1,3-dibutyl-1,1,3,3-tetramethyldisiloxane; and
hexylpentamethyldisiloxane;

b) the following trisiloxanes:
octamethyltrisiloxane (surface tension=17.4 mN/m), sold, for example, under the name DC 200 Fluid 1 cst by the company Dow Corning;
3-pentyl-1,1,1,3,5,5,5-heptamethyltrisiloxane;
1-hexyl-1,1,3,3,5,5,5-heptamethyltrisiloxane;
1,1,1,3,3,5,5-heptamethyl-5-octyltrisiloxane;
1,1,1,3,5,5,5-heptamethyl-3-octyltrisiloxane, sold, for example, under the name "Silsoft 034" by the company OSI;
1,1,1,3,5,5,5-heptamethyl-3-hexyltrisiloxane (surface tension=20.5 mN/m), sold, for example, under the name "DC2-1731" by the company Dow Corning;
1,1,3,3,5,5-hexamethyl-1,5-dipropyltrisiloxane;
3-(1-ethylbutyl)-1,1,1,3,5,5,5-heptamethyltrisiloxane;
1,1,1,3,5,5,5-heptamethyl-3-(1-methylpentyl)trisiloxane;
1,5-diethyl-1,1,3,3,5,5-hexamethyltrisiloxane;
1,1,1,3,5,5,5-heptamethyl-3-(1-methylpropyl)trisiloxane;
3-(1,1-dimethylethyl)-1,1,1,3,5,5,5-heptamethyltrisiloxane;
1,1,1,5,5,5-hexamethyl-3,3-bis(1-methylethyl)trisiloxane;
1,1,1,3,3,5,5-hexamethyl-1,5-bis(1-methylpropyl)trisiloxane;
1,5-bis(1,1-dimethylethyl)-1,1,3,3,5,5-hexamethyltrisiloxane;
3-(3,3-dimethylbutyl)-1,1,1,3,5,5,5-heptamethyltrisiloxane;
1,1,1,3,5,5,5-heptamethyl-3-(3-methylbutyl)trisiloxane;
1,1,1,3,5,5,5-heptamethyl-3-(3-methylpentyl)trisiloxane;
1,1,1,3,5,5,5-heptamethyl-3-(2-methylpropyl)trisiloxane;
1-butyl-1,1,3,3,5,5,5-heptamethyltrisiloxane;
1,1,1,3,5,5,5-heptamethyl-3-propyltrisiloxane;
3-isohexyl-1,1,1,3,5,5,5-heptamethyltrisiloxane;
1,3,5-triethyl-1,1,3,5,5-pentamethyltrisiloxane;
3-butyl-1,1,1,3,5,5,5-heptamethyltrisiloxane;
3-tert-pentyl-1,1,1,3,5,5,5-heptamethyltrisiloxane;
1,1,1,5,5,5-hexamethyl-3,3-dipropyltrisiloxane;
3,3-diethyl-1,1,1,5,5,5-hexamethyltrisiloxane;
1,5-dibutyl-1,1,3,3,5,5-hexamethyltrisiloxane;
1,1,5,5,5-hexaethyl-3,3-dimethyltrisiloxane;
3,3-dibutyl-1,1,1,5,5,5-hexamethyltrisiloxane;
3-ethyl-1,1,1,3,5,5,5-heptamethyltrisiloxane;
3-heptyl-1,1,1,3,5,5,5-heptamethyltrisiloxane; and
1-ethyl-1,1,3,3,5,5,5-heptamethyltrisiloxane;

c) the following tetrasiloxanes:
decamethyltetrasiloxane (surface tension=18 mN/m), sold, for example, under the name DC 200 Fluid 1.5 cst by the company Dow Corning;
1,1,3,3,5,5,7,7-octamethyl-1,7-dipropyltetrasiloxane;
1,1,1,3,3,5,7,7,7-nonamethyl-5-(1-methylethyl)tetrasiloxane;
1-butyl-1,1,3,3,5,5,7,7,7-nonamethyltetrasiloxane;
3,5-diethyl-1,1,1,3,5,7,7,7-octamethyltetrasiloxane;
1,3,5,7-tetraethyl-1,1,3,5,7,7-hexamethyltetrasiloxane;
3,3,5,5-tetraethyl-1,1,1,7,7,7-hexamethyltetrasiloxane;
1,1,1,3,3,5,5,7,7-nonamethyl-7-phenyltetrasiloxane;
3,3-diethyl-1,1,1,5,5,7,7,7-octamethyltetrasiloxane; and
1,1,1,3,3,5,7,7,7-nonamethyl-5-phenyltetrasiloxane;

d) the following pentasiloxanes:
dodecamethylpentasiloxane (surface tension=18.7 mN/m), sold, for example, under the name DC 200 Fluid 2 cst by the company Dow Corning;
1,1,3,3,5,5,7,7,9,9-decamethyl-1,9-dipropylpentasiloxane;
3,3,5,5,7,7-hexaethyl-1,1,1,9,9,9-hexamethylpentasiloxane;
1,1,1,3,3,5,7,7,9,9,9-undecamethyl-5-phenylpentasiloxane;
1-butyl-1,1,3,3,5,5,7,7,9,9,9-undecamethylpentasiloxane;
3,3-diethyl-1,1,1,5,5,7,7,9,9,9-decamethylpentasiloxane;
1,3,5,7,9-pentaethyl-1,1,3,5,7,9,9-heptamethylpentasiloxane;
3,5,7-triethyl-1,1,3,5,7,9,9,9-nonamethylpentasiloxane; and
1,1,1-triethyl-3,3,5,5,7,7,9,9,9-nonamethylpentasiloxane;

e) the following hexasiloxanes:
1-butyl-1,1,3,3,5,5,7,7,9,9,11,11,11-tridecamethylhexasiloxane;

3,5,7,9-tetraethyl-1,1,1,3,5,7,9,11,11,11-decamethylhexasiloxane; and tetradecamethylhexasiloxane;
f) hexadecamethylheptasiloxane; and
g) octadecamethyloctasiloxane.

Among the silicones of formula (II) that may be mentioned are, for example:
a) the following tetrasiloxanes:
2-[3,3,3-trimethyl-1,1-bis[(trimethylsilyl)oxy]disiloxanyl]ethyl;
1,1,1,5,5,5-hexamethyl-3-(2-methylpropyl)-3-[(trimethylsilyl)oxy]trisiloxane;
3-(1,1-dimethylethyl)-1,1,1,5,5,5-hexamethyl-3-[(trimethylsilyl)oxy]trisiloxane;
3-butyl-1,1,1,5,5,5-hexamethyl-3-[(trimethylsilyl)oxy]trisiloxane;
1,1,1,5,5,5-hexamethyl-3-propyl-3-[(trimethylsilyl)oxy]trisiloxane;
3-ethyl-1,1,1,5,5,5-hexamethyl-3-[(trimethylsilyl)oxy]trisiloxane;
1,1,1-triethyl-3,5,5,5-hetramethyl-3-(trimethylsiloxy)trisiloxane;
3-methyl-1,1,1,5,5,5-hexamethyl-3-[trimethylsilyl)oxy]trisiloxane;
3-[(dimethylphenylsilyl)oxy]-1,1,1,3,5,5,5-heptamethyltrisiloxane;
1,1,1,5,5,5-hexamethyl-3-(2-methylpentyl)-3-[(trimethylsilyl)oxy]trisiloxane;
1,1,1,5,5,5-hexamethyl-3-(4-methylpentyl)-3-[(trimethylsilyl)oxy]trisiloxane;
3-hexyl-1,1,1,5,5,5-hexamethyl-3-[(trimethylsilyl)oxy]trisiloxane; and
1,1,1,3,5,5,5-heptamethyl-3-[(trimethylsilyl)oxy]trisiloxane;
b) the following pentasiloxanes:
1,1,1,3,5,5,7,7,7-nonamethyl-3-(trimethylsiloxy)tetrasiloxane; and
1,1,1,3,3,7,7,7-octamethyl-5-phenyl-5-[(trimethylsilyl)oxy]tetrasiloxane; and
c) the following heptasiloxanes:
1,1,1,3,5,5,7,7,9,9,11,11,11-tridecamethyl-3-[(trimethylsilyl)oxy]hexasiloxane.

Among the silicones of formula (III) that may be mentioned is, for example:
1,1,1,5,5,5-hexamethyl-3,3-bis(trimethylsiloxy)trisiloxane.

It is also possible to use other volatile silicone oils chosen, for example, from:
a) the following tetrasiloxanes:
2,2,8,8-tetramethyl-5-[(pentamethyldisiloxanyl)methyl]-3,7-dioxa-2,8-disilanonane;
2,2,5,8,8-pentamethyl-5-[(trimethylsilyl)methoxy]4,6-dioxa-2,5,8-trisilanonane;
1,3-dimethyl-1,3-bis[(trimethylsilyl)methyl]-1,3-disiloxanediol;
3-ethyl-1,1,1,5,5,5-hexamethyl-3-[3-(trimethylsiloxy)propyl]trisiloxane; and
1,1,1,5,5,5-hexamethyl-3-phenyl-3-[(trimethylsilyl)oxy]trisiloxane (Dow 556 Fluid);
b) the following pentasiloxanes:
2,2,7,7,9,9,11,11,16,16-decamethyl-3,8,10,15-tetraoxa-2,7,9,11,16-pentasilaheptadecane; and
tetrakis[(trimethylsilyl)methyl] of silicic acid ester;
c) the following hexasiloxanes:
3,5-diethyl-1,1,1,7,7,7-hexamethyl-3,5-bis[(trimethylsilyl)oxy]tetrasiloxane; and
1,1,1,3,5,7,7,7-octamethyl-3,5-bis[(trimethylsilyl)oxy]tetrasiloxane;

d) heptasiloxane:
1,1,1,3,7,7,7-heptamethyl-3,5,5-tris[(trimethylsilyl)oxy]tetrasiloxane; and
e) the following octasiloxanes:
1,1,3,5,5,9,9,9-nonamethyl-3,7,7-tris[(trimethylsilyl)oxy]pentasiloxane;
1,1,1,3,5,7,9,9,9-nonamethyl-3,5,7-tris[(trimethylsilyl)oxy]pentasiloxane; and
1,1,1,7,7,7-hexamethyl-3,3,5,5-tetrakis[(trimethylsilyl)oxy]tetrasiloxane.

In one embodiment, the volatile silicone oils that may be used include: decamethyltetrasiloxane; dodecamethylpentasiloxane;
3-butyl-1,1,1,3,5,5,5-heptamethyltrisiloxane;
1,1,1,3,5,5,5-heptamethyl-3-hexyltrisiloxane;
and mixtures thereof.

The volatile fatty phase of the composition disclosed herein may, for example, comprise a mixture of dodecamethylpentasiloxane and decamethyltetrasiloxane, which may be present in a dodecamethylpentasiloxane/decamethyltetrasiloxane weight ratio ranging, for example, from 55/45 to 80/20, such as from 60/40 to 75/25, further such as from 60/40 to 70/30.

Further disclosed herein is a composition comprising, in a physiologically acceptable medium, a volatile silicone fatty phase comprising a mixture of dodecamethylpentasiloxane and decamethyltetrasiloxane in a dodecamethylpentasiloxane/decamethyltetrasiloxane weight ratio ranging from 55/45 to 80/20, such as from 60/40 to 75/25 and further such as from 60/40 to 70/30.

For example, the volatile silicone fatty phase of the composition may be formed essentially, or even solely, from the mixture of dodecamethylpentasiloxane and decamethyltetrasiloxane described above.

According to another embodiment disclosed herein, the volatile fatty phase comprises a mixture of dodecamethylpentasiloxane and 3-butyl-1,1,1,3,5,5,5-heptamethyltrisiloxane in a dodecamethylpentasiloxane/3-butyl-1,1,1,3,5,5,5-heptamethyltrisiloxane weight ratio ranging, for example, from 75/25 to 50/50, such as from 70/30 to 55/45 and further such as from 65/35 to 55/45.

Also disclosed herein is a composition comprising, in a physiologically acceptable medium, a volatile silicone fatty phase comprising a mixture of dodecamethylpentasiloxane and 3-butyl-1,1,1,3,5,5,5-heptamethyltrisiloxane in a dodecamethylpentasiloxane/3-butyl-1,1,1,3,5,5,5-heptamethyltrisiloxane weight ratio ranging from 75/25 to 50/50, such as from 70/30 to 55/45, and further such as from 65/35 to 55/45.

For example, the volatile silicone fatty phase of the composition may be formed essentially, or even solely, of the mixture of dodecamethylpentasiloxane and 3-butyl-1,1,1,3,5,5,5-heptamethyltrisiloxane described above.

According to another embodiment disclosed herein, the volatile fatty phase comprises a mixture of decamethyltetrasiloxane and 1,1,1,3,5,5,5-heptamethyl-3-hexyltrisiloxane, in a decamethyltetrasiloxane/1,1,1,3,5,5,5-heptamethyl-3-hexyltrisiloxane weight ratio ranging, for example, from 25/75 to 45/55, such as from 30/70 to 40/60 and further such as from 35/65 to 40/60.

Further disclosed herein is a composition comprising, in a physiologically acceptable medium, a volatile silicone fatty phase comprising a mixture of decamethyltetrasiloxane and 1,1,1,3,5,5,5-heptamethyl-3-hexyltrisiloxane in a decamethyltetrasiloxane/1,1,1,3,5,5,5-heptamethyl-3-hexyltrisiloxane weight ratio ranging from 25/75 to 45155, such as from 30/70 to 40/60 and further such as from 35/65 to 40/60.

For example, the volatile silicone fatty phase of the composition may be formed essentially, or even solely, of the mixture of decamethyltetrasiloxane and 1,1,1,3,5,5,5-heptamethyl-3-hexyltrisiloxane described above.

According to another embodiment disclosed herein, the volatile fatty phase comprises a mixture of 3-hexyl-1,1,1,3,5,5,5-heptamethyltrisiloxane and 3-butyl-1,1,1,3,5,5,5-heptamethyltrisiloxane in a 3-hexyl-1,1,1,3,5,5,5-heptamethyltrisiloxane/3-butyl-1,1,1,3,5,5,5-heptamethyltrisiloxane weight ratio ranging, for example, from 45/55 to 70/30, such as from 50/50 to 65/35 and further such as from 55/45 to 60/40.

Further disclosed herein is a composition comprising, in a physiologically acceptable medium, a volatile silicone fatty phase comprising a mixture of 3-hexyl-1,1,1,3,5,5,5-heptamethyltrisiloxane and 3-butyl-1,1,1,3,5,5,5-heptamethyltrisiloxane in a 3-hexyl-1,1,1,3,5,5,5-heptamethyltrisiloxane/3-butyl-1,1,1,3,5,5,5-heptamethyltrisiloxane weight ratio ranging from 45/55 to 70/30, such as from 50/50 to 65/35 and further such as from 55/45 to 60/40.

For example, the volatile silicone fatty phase of the composition may be formed essentially, or even solely, of the mixture of 3-hexyl-1,1,1,3,5,5,5-heptamethyltrisiloxane and 3-butyl-1,1,1,3,5,5,5-heptamethyltrisiloxane described above.

According to one embodiment disclosed herein, the volatile silicone fatty phase of the composition comprises from 0 to 5% by weight, such as from 0 to 1% by weight, of at least one volatile cyclic silicone oil, relative to the total weight of the volatilesilicone fatty phase.

The at least one non-cyclic volatile silicone oil may be present in an amount ranging from 1% to 80% by weight, such as from 1% to 65% by weight and further such as from 1% to 50% by weight, relative to the total weight of the composition.

The composition disclosed herein may also comprise at least one volatile non-silicone oil chosen, for example, from volatile hydrocarbon-based and fluoro oils.

The term "hydrocarbon-based oil" means an oil formed essentially, or even solely, of carbon and hydrogen atoms, and optionally of oxygen and nitrogen atoms, and containing no silicon or fluorine atoms. It may comprise at least one group chosen from alcohol, ester, ether, carboxylic acid, amine and amide groups.

The volatile hydrocarbon-based oil may be chosen from volatile hydrocarbon-based oils comprising from 8 to 16 carbon atoms and mixtures thereof, such as $C_8$-$C_{16}$ branched alkanes, for instance $C_8$-$C_{16}$ isoalkanes (also known as isoparaffins), isododecane, isodecane, isohexadecane and, for example, the oils sold under the trade names "Isopars" or "Permethyls", $C_8$-$C_{16}$ branched esters, for instance isohexyl neopentanoate, and mixtures thereof; in one embodiment, isododecane is used.

The at least one non-silicone volatile oil may be present in an amount ranging from 0.1% to 50% by weight, such as from 0.1% to 40% by weight and further such as from 0.1% to 30% by weight, relative to the total weight of the composition.

The composition disclosed herein may also comprise at least one non-volatile oil.

The at least one non-volatile oil may be chosen, for example, from hydrocarbon-based oils of mineral origin and synthetic origin, such as linear and branched hydrocarbons, for instance liquid paraffin and derivatives thereof, liquid petroleum jelly, polydecenes, hydrogenated polyisobutene such as Parleam sold by the company Nippon Oil Fats, and squalane of synthetic origin and plant origin; oils of animal origin, for instance mink oil, turtle oil and perhydrosqualene; hydrocarbon-based oils of plant origin with a high triglyceride content comprising fatty acid esters of glycerol, the fatty acids of which may have varying chain lengths, these chains possibly being linear or branched, and saturated or unsaturated, such as fatty acid triglycerides comprising, for example, from 4 to 22 carbon atoms, for instance heptanoic and octanoic acid triglycerides, and capric/caprylic acid triglyceride, and hydroxylated triglycerides, such as sweet almond oil, beauty-leaf oil, palm oil, grapeseed oil, sesame oil, arara oil, rapeseed oil, sunflower oil, cotton oil, apricot oil, castor oil, alfalfa oil, marrow oil, blackcurrant oil, macadamia oil, musk rose oil, hazelnut oil, avocado oil, jojoba oil, olive oil, cereal (maize, wheat, barley or rye) germ oil, and karite butter; fatty acid esters, such as those comprising from 4 to 22 carbon atoms, and for example, fatty acid esters of octanoic acid, of heptanoic acid, of lanolic acid, of oleic acid, of lauric acid and of stearic acid, for instance propylene glycol dioctanoate, propylene glycol monoisostearate, polyglyceryl-2 diisostearate and neopentylglycol diheptanoate; synthetic esters of formula $R_1COOR_2$ in which $R_1$ is chosen from linear and branched higher fatty acid residues comprising from 7 to 40 carbon atoms and $R_2$ is chosen from branched hydrocarbon-based chains comprising from 3 to 40 carbon atoms, for instance purcellin oil (cetostearyl octanoate), isononyl isononanoate, $C_{12}$ to $C_{15}$ alkyl benzoate, 2-ethylhexyl palmitate, 2-octyldodecyl stearate, 2-octyldodecyl erucate, isostearyl isostearate, 2-octyidodecyl benzoate, alkyl and polyalkyl octanoates, decanoates and ricinoleates, isopropyl myristate, isopropyl palmitate, butyl stearate, hexyl laurate, diisopropyl adipate, 2-ethylhexyl palmitate, 2-hexyldecyl laurate, 2-octyldecyl palmitate, 2-octyidodecyl myristate, 2-diethylhexyl succinate, diisostearyl malate and isodecyl neopentanoate; hydroxylated esters, for instance isostearyl lactate, octyl hydroxystearate, octyidodecyl hydroxystearate, diisostearyl malate, triisocetyl citrate, glyceryl triisostearate and diglyceryl triisostearate; diethylene glycol diisononanoate; pentaerythritol esters; esters of aromatic acids and of alcohols comprising from 4 to 22 carbon atoms, such as tridecyl trimellitate; $C_8$-$C_{26}$ higher fatty acids such as oleic acid, linoleic acid, linolenic acid and isostearic acid; $C_8$-$C_{26}$ higher fatty alcohols such as oleyl alcohol, linoleyl alcohol, linolenyl alcohol, isostearyl alcohol or octyldodecanol; synthetic esters comprising at least 7 carbon atoms, silicone oils such as polydimethylsiloxanes (PDMS) that are liquid at room temperature, linear, and optionally phenylated, such as phenyltrimethicones, phenyltrimethylsiloxydiphenyl-siloxanes, diphenyl dimethicones, diphenylmethyldiphenyltrisiloxanes, liquid 2-phenylethyl trimethylsiloxysilicates, optionally substituted with at least one group chosen from aliphatic and aromatic groups, for instance alkyl, alkoxy and phenyl groups, which are pendent and/or at the end of a silicone chain, these groups comprising from 2 to 24 carbon atoms and being optionally fluorinated, and chosen from functional groups such as hydroxyl, thiol and amine groups; polysiloxanes modified with fatty acids, fatty alcohols and polyoxyalkylenes, for instance dimethicone copolyols and alkylmethicone copolyols; liquid fluorosilicones; and mixtures thereof.

The at least one non-volatile oil may be present in an amount ranging from 0.1% to 60% by weight, such as from 0.5% to 50% by weight and further such as from 1% to 40% by weight, relative to the total weight of the composition.

The composition disclosed herein may further comprise at least one aqueous phase containing water. The water may be chosen from, for example, floral water such as cornflower water and mineral water such as eau de Vittel, eau de Lucas and eau de La Roche Posay and spring water.

The at least one aqueous phase may also comprise at least one organic solvent that is miscible with water (at 25° C.), chosen, for example, from primary alcohols such as ethanol and isopropanol, glycols such as glycerol, propylene glycol, butylene glycol, dipropylene glycol, diethylene glycol, glycol ethers, $C_1$ to $C_4$ alkyl ethers of mono-di- and tripropylene glycols, and mono-, di- and triethylene glycols.

The composition may be an anhydrous composition, i.e., a composition containing less than 2% by weight of water, or even less than 0.5% of water, such as water-free, the water not being added during the preparation of the composition but corresponding to the residual water provided by the ingredients mixed therein.

The composition may comprise at least one additional ingredient chosen from common cosmetic and dermatological ingredients that may be chosen, for example, from polymers, such as film-forming polymers and fixing polymers; surfactants; hair conditioners; dyestuffs; nacreous agents; opacifiers; organic solvents; fragrances; thickeners; gelling agents; waxes; pasty products; hair dyes; silicone resins; silicone gums; preserving agents; antioxidants; cosmetic active agents; sunscreens; pH stabilizers; vitamins; moisturizers; antiperspirants; deodorants; self-tanning compounds; and mixtures thereof.

Needless to say, a person skilled in the art will take care to select this or these optional additional compound(s), and/or the amount thereof, such that the advantageous properties of the composition disclosed herein are not, or are not substantially, adversely affected by the envisaged addition.

The composition may also comprise, for example, at least one dyestuff chosen, for example, from lipophilic dyes, hydrophilic dyes, pigments and nacres usually used in cosmetic and dermatological compositions. The at least one dyestuff may be present in an amount ranging from 0.01% to 40%, such as from 1% to 35% and further such as from 5% to 25%, relative to the total weight of the composition.

The composition disclosed herein may be in liquid, pasty or solid form, or in the form of a mousse or a spray. It may be an emulsion or an anhydrous composition.

The composition disclosed herein may be used for making up, caring for or cleansing human keratin materials such as the skin (of the face, the body, the scalp or the lips), mucous membranes (inner edge of the eyelids), the hair, the nails, the eyelashes and/or the eyebrows.

The composition thus finds application as a care composition for the body and/or the face; a cleansing composition for the body and/or the face, such as a shower gel, a bath gel or a makeup remover; a makeup composition for the body and/or the face, such as a foundation, a lipstick, a lipcare product, a nail varnish, a nailcare product, a mascara or an eyeliner; a fragrancing composition; a hair composition such as a hair dye composition or a permanent-reshaping hair composition; an antisun composition; a deodorant composition; a haircare and/or hair cleansing composition, such as a shampoo, a rinse-out or leave-in conditioner, a rinse-out composition to be applied before or after dyeing, bleaching, permanent-waving or relaxing the hair or between the two steps of a permanent-waving or relaxing operation; a hair composition for holding the hairstyle, such as a styling lacquer, gel, mousse or spray.

The processes for manufacturing the products disclosed herein do not differ in any way from the processes conventionally used in cosmetics and are entirely familiar to those skilled in the art.

Embodiments disclosed herein are illustrated in greater detail by means of the non-limiting examples described below.

Measurement of the Rate of Evaporation of an Oil:

15 g of oil or of the mixture of oils to be tested are placed in a crystallizing dish (diameter: 7 cm) placed on a balance that is inside a chamber of about 0.3 $m^3$ with a regulated temperature (25° C.) and a regulated hygrometry (50% relative humidity). The liquid is allowed to evaporate freely, without stirring, while providing ventilation with a fan (Papst-Motoren, reference 8550 N, rotating at 2700 rpm) positioned vertically above the crystallizing dish containing the solvent, the vanes facing the crystallizing dish and being 20 cm from the bottom of the crystallizing dish. The mass of oil remaining in the crystallizing dish is measured at regular intervals. The evaporation rates are expressed in mg of oil evaporated per unit of surface area ($cm^2$) and per unit of time (minutes).

Measurement of the Surface Tension of a Volatile Oil:

The surface tension is determined by the "hanging drop" method. It is measured at 25±1° C. using a Fibro DAT 1100 tensiometer, sold by the company Fibro (Sweden). A drop of volatile oil is formed using a syringe controlled by the tensiometer at the outlet of a Teflon cannula with an inside diameter of 200 μm and an outside diameter of 1.5 mm, held in a vertical position. The volume of the drop is from 1 to 10 microliters such as from 5 to 10 microliters. The hanging drop is observed using a camera integrated into the measuring device, and its shape is parametized by the software of the Fibro DAT 1100 tensiometer using a resolution method of the Laplace equation. The result is given in mN/m.

EXAMPLE 1

A foundation in the form of a water-in-oil emulsion having the composition below was prepared:

| | |
|---|---:|
| Cetyldimethicone copolyol | 3 g |
| (Abil EM 90 from the company Goldschmidt) | |
| Isostearyl diglyceryl succinate | 0.6 g |
| (Imwitor 780K from the company Condea) | |
| Decamethyltetrasiloxane | 6.48 g |
| (DC 200 Fluid 1.5 cst from Dow Corning) | |
| Dodecamethylpentasiloxane | 12.02 g |
| (DC 200 Fluid 2 cst from Dow Corning) | |
| Isododecane | 7.1 g |
| Mixture of pigments | 10 g |
| (hydrophobic iron oxides and titanium oxides) | |
| Bentone | 1.6 g |
| Polyamide powder(Nylon-12 from Dupont de Nemours) | 8 g |
| Magnesium sulphate | 0.7 g |
| Preserving agent | 0.45 g |
| Fragrance | 0.5 g |
| Water | qs 100 g |

EXAMPLE 2

An oil-in-water foundation having the composition below was prepared:

| | |
|---|---:|
| Decamethyltetrasiloxane | 3.3 g |
| (DC 200 Fluid 1.5 cst from Dow Corning) | |
| Dodecamethylpentasiloxane | 7.7 g |
| (DC 200 Fluid 2 cst from Dow Corning) | |
| Hydrogenated polyisobutene (Parleam, NOF Corporation) | 5 g |
| 2-Ethylhexyl palmitate | 11 g |
| Glyceryl isostearate | 4 g |
| Stearic acid | 2 g |
| Triethanolamine | 1 g |

| | |
|---|---|
| Polyamide powder (Nylon-12 from Dupont de Nemours) | 5 g |
| Mixture of pigments (iron oxides and titanium oxides) | 10 g |
| Carboxymethylcellulose | 0.2 g |
| Propylene glycol | 5 g |
| Glycerol | 2 g |
| Fragrance | 0.5 g |
| Preserving agents | 0.4 g |
| Water | qs 100 g |

EXAMPLE 3

A lipstick having the composition below was prepared:

| | |
|---|---|
| Polyethylene wax (Performalene 655, New Phase Technologies) | 20 g |
| Decamethyltetrasiloxane (DC 200 Fluid 1.5 cst from Dow Corning) | 18.2 g |
| Dodecamethylpentasiloxane (DC 200 Fluid 2 cst from Dow Corning) | 4 g |
| Cyclopentadimethylsiloxane (DC 245 Fluid from Dow Corning) | 6 g |
| Isododecane | 51.8 g |
| DC Red No. 7 Calcium Lake (pigment) | 6 g |

EXAMPLE 4

A care cream having the composition below was prepared:
Fatty Phase:
Mixture of glyceryl monostearate and of polyethylene glycol stearate 100 EO (50/50 by weight)

| | |
|---|---|
| (Arlacel 165 from the company ICI) | 2.5 g |
| Stearyl alcohol | 0.5 g |
| Stearic acid | 1 g |
| Hydrogenated polyisobutene (Parleam, NOF Corporation) | 9 g |
| Decamethyltetrasiloxane (DC 200 Fluid 1.5 cst from Dow Corning) | 2.1 g |
| Dodecamethylpentasiloxane (DC 200 Fluid 2 cst from Dow Corning) | 2.1 g |

Aqueous Phase

| | |
|---|---|
| Crosslinked polyacrylic acid (Carbopol 980) | 1 g |
| Triethanolamine | 0.03 g |
| Preserving agent | 0.3 g |
| Water | qs 100 g |

EXAMPLE 5

A makeup remover having the composition below was prepared:

| | |
|---|---|
| Isopropyl palmitate | 8 g |
| Decamethyltetrasiloxane (DC 200 Fluid 1.5 cst from Dow Corning) | 2.8 g |
| Dodecamethylpentasiloxane (DC 200 Fluid 2 cst from Dow Corning) | 5.2 g |
| Stearyl alcohol | 8 g |
| Sucrose stearate | 2 g |
| Stearic acid | 0.3 g |
| Sodium hydroxide | 0.06 g |
| Glycerol | 5 g |
| Carbopol | 0.2 g |
| Water | qs 100 g |

What is claimed is:

1. A composition comprising, in a physiologically acceptable medium, a volatile silicone fatty phase comprising a mixture of dodecamethylpentasiloxane and decamethyltetrasiloxane, wherein at least one of the dodecamethylpentasiloxane and the decamethyltetrasiloxane has a surface tension of less than 21 mN/m and wherein the volatile silicone fatty phase has an evaporation profile such that the mass of the mixture of dodecamethylpentasiloxane and decamethyltetrasiloxane evaporated after 30 minutes ranges from 2 mg/cm$^2$ to 9 mg/cm$_2$.

2. The composition according to claim 1, wherein the dodecamethylpentasiloxane and the decamethyltetrasiloxane are present in a dodecamethylpentasiloxane/decamethyltetrasiloxane weight ratio ranging from 55/45 to 80/20.

3. The composition according to claim 2, wherein the dodecamethylpentasiloxane/decamethyltetrasiloxane weight ratio ranges from 60/40 to 75/25.

4. The composition according to claim 3, wherein the dodecamethylpentasiloxane/decamethyltetrasiloxane weight ratio ranges from 60/40 to 70/30.

5. A composition comprising, in a physiologically acceptable medium, a volatile silicone fatty phase comprising a mixture of dodecamethylpentasiloxane and decamethyltetrasiloxane in a dodecamethylpentasiloxane/decamethyltetrasiloxane weight ratio ranging from 55/45 to 80/20, wherein at least one of the dodecamethylpentasiloxane and the decamethyltetrasiloxane has a surface tension of less than 21 mN/m.

6. The composition according to claim 5, wherein the dodecamethylpentasiloxane/decamethyltetrasiloxane weight ratio ranges from 60/40 to 75/25.

7. The composition according to claim 6, wherein the dodecamethylpentasiloxane/decamethyltetrasiloxane weight ratio ranges from 60/40 to 70/30.

8. The composition according to claim 1, wherein the volatile silicone fatty phase comprises from 0 to 5% by weight of at least one cyclic volatile silicone oil, relative to the total weight of the volatile silicone fatty phase.

9. The composition according to claim 8, wherein the volatile silicone fatty phase comprises from 0 to 1% by weight of at least one cyclic volatile silicone oil, relative to the total weight of the volatile silicone fatty phase.

10. The composition according to claim 1, wherein the dodecamethylpentasiloxane and the decamethyltetrasiloxane are present in an amount ranging form 1% to 80% by weight, relative to the total weight of the composition.

11. The composition according to claim 10, wherein the dodecamethylpentasiloxane and the decamethyltetrasiloxane are present in an amount ranging from 1% to 65% by weight, relative to the total weight of the composition.

12. The composition according to claim 11, wherein the dodecamethylpentasiloxane and the decamethyltetrasiloxane are present in an amount ranging from 1% to 50% by weight, relative to the total weight of the composition.

13. The composition according to claim 1, further comprising at least one volatile non-silicone oil.

14. The composition according to claim 13, wherein the at least one non-silicone volatile oil is chosen from volatile hydrocarbon-based oils.

15. The composition according to claim 14, wherein the hydrocarbon-based volatile oils are chosen from isododecane, isodecane, isohexadecane and isohexyl neopentanoate, and mixtures thereof.

16. The composition according to claim 13, wherein the at least one volatile non-silicone oil is present in an amount ranging from 0.1% to 50% by weight, relative to the total weight of the composition.

17. The composition according to claim 16, wherein the at least one volatile non-silicone oil is present in an amount ranging from 0.1% to 40% by weight, relative to the total weight of the composition.

18. The composition according to claim 17, wherein the at least one volatile non-silicone oil is present in an amount ranging from 0.1% to 30% by weight, relative to the total weight of the composition.

19. The composition according to claim 1, further comprising at least one non-volatile oil.

20. The composition according to claim 19, wherein the at least one non-volatile oil is present in an amount ranging from 0.1% to 60% by weight, relative to the total weight of the composition.

21. The composition according to claim 20, wherein the at least one non-volatile oil is present in an amount ranging from 0.5% to 50% by weight, relative to the total weight of the composition.

22. The composition according to claim 21, wherein the at least one non-volatile oil is present in an amount ranging from 1% to 40% by weight, relative to the total weight of the composition.

23. The composition according to claim 1, further comprising at least one additional ingredient chosen from cosmetic and dermatological ingredients chosen from film-forming polymers and fixing polymers; surfactants; hair conditioners; dyestuffs; nacreous agents; opacifiers; organic solvents; fragrances; thickeners; gelling agents; waxes; pasty products; hair dyes; silicone resins; silicone gums; preserving agents; antioxidants; cosmetic active agents; sunscreens; pH stabilizers; vitamins; moisturizers; antiperspirants; deodorants; and self-tanning compounds.

24. The composition according to claim 1, wherein the composition is in a form chosen from care compositions for body and face; cleansing compositions for the body and the face; makeup compositions for the body and the face; fragrancing compositions; hair compositions; antisun compositions; antiperspirants; deodorants; haircare and hair cleansing compositions; and hair compositions for holding hairstyle.

25. The composition according to claim 24, wherein the cleansing compositions for the body and the face are chosen from shower gels, bath gels, and makeup removers.

26. The composition according to claim 24, wherein the makeup compositions for the body and the face are chosen from foundations, lipsticks, lipcare products, nail varnishes, nailcare products, mascaras and eyeliners.

27. The composition according to claim 24, wherein the hair compositions are chosen from hair dye compositions and permanent-reshaping hair compositions.

28. The composition according to claim 24, wherein the haircare and hair cleansing compositions are chosen from shampoos, rinse-out conditioners, leave-in conditioners, rinse-out compositions to be applied before or after dyeing, bleaching, permanent-waving or relaxing the hair or between the two steps of a permanent-waving or relaxing operation.

29. The composition according to claim 24, wherein the hair compositions for holding hairstyle are chosen from styling lacquers, styling gels, styling mousses, and styling sprays.

* * * * *

UNITED STATES PATENT AND TRADEMARK OFFICE
CERTIFICATE OF CORRECTION

PATENT NO. : 8,440,211 B2
APPLICATION NO. : 12/277742
DATED : May 14, 2013
INVENTOR(S) : Frédéric Auguste It is certified that error appears in the above-identified patent and that said Letters Patent is hereby corrected as shown below:

Title Page, Item (75), Inventor's name should read --Frédéric Auguste--.

In the Claims:

Column 12, line 18, "9 mg/cm$_2$" should read --9 mg/cm$^2$--;

line 53, "form 1%" should read --from 1%--.

Signed and Sealed this
Sixteenth Day of July, 2013

Teresa Stanek Rea
*Acting Director of the United States Patent and Trademark Office*